(12) United States Patent
Hall

(10) Patent No.: US 8,764,443 B2
(45) Date of Patent: Jul. 1, 2014

(54) METHOD FOR PRODUCING A SURFACE STRUCTURE ON AN IMPLANT, AND SUCH AN IMPLANT

(75) Inventor: Jan Hall, Gothenburg (SE)

(73) Assignee: Nobel Biocare Services AG, Glattbrugg (CH)

( * ) Notice: Subject to any disclaimer, the term of this patent is extended or adjusted under 35 U.S.C. 154(b) by 1414 days.

(21) Appl. No.: 10/499,430

(22) PCT Filed: Dec. 18, 2002

(86) PCT No.: PCT/SE02/02361
§ 371 (c)(1),
(2), (4) Date: Feb. 7, 2005

(87) PCT Pub. No.: WO03/055405
PCT Pub. Date: Jul. 10, 2003

(65) Prior Publication Data
US 2005/0147942 A1    Jul. 7, 2005

(30) Foreign Application Priority Data

Dec. 21, 2001 (SE) ........................ 0104350

(51) Int. Cl.
*A61C 8/00* (2006.01)
(52) U.S. Cl.
USPC ........................ 433/173; 433/201.1
(58) Field of Classification Search
USPC ............. 433/172–176, 201.1, 215, 220, 221; 470/10; 606/73; 623/16.11
See application file for complete search history.

(56) References Cited

U.S. PATENT DOCUMENTS

| 1,698,951 A | 1/1929 | Holmes |
| 2,215,770 A | 9/1940 | Sheffield |
| 3,672,058 A | 6/1972 | Nikoghossian |

(Continued)

FOREIGN PATENT DOCUMENTS

| DE | 4130891 | 3/1992 |
| DE | 10231 743 A1 | 2/2004 |

(Continued)

OTHER PUBLICATIONS

Translation of FR 2610512.*

(Continued)

*Primary Examiner* — Heidi M Eide
(74) *Attorney, Agent, or Firm* — Knobbe, Martens, Olson & Bear, LLP.

(57) ABSTRACT

A surface structure is produced on an outer surface of an implant or a fixture and forms a base structure in a range of implants related to different types and qualities of jaw bone. During production of the surface, parts of a turning tool are placed against the implant or against a blank which is intended to form the implant. The parts and/or the implant are assigned controls which give rise to mutual displacements between the parts and the implant so that the parts follow a substantially spiral trajectory along the outer surface. By means of said controls, a long wave pattern is formed with successive peaks and with through lying between these. In this connection, a through can be arranged adjacent to the outer parts of an existing thread. The controls are chosen so as to produce through depths in the range of 25 to 250 µm, preferably 50 to 200 µm. The invention also relates to an implant which has the same character as the implant produced by the method.

33 Claims, 3 Drawing Sheets

(56) References Cited

U.S. PATENT DOCUMENTS

Figure 4:
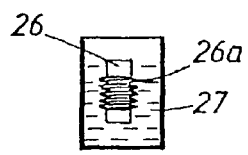

| | | | |
|---|---|---|---|
| 3,797,113 A | 3/1974 | Brainin | |
| 3,849,887 A | 11/1974 | Brainin | |
| 4,103,422 A * | 8/1978 | Weiss et al. | 433/215 |
| 4,406,623 A | 9/1983 | Grafelmann et al. | |
| 4,431,416 A | 2/1984 | Niznick | |
| 4,468,200 A | 8/1984 | Munch | |
| 4,547,157 A | 10/1985 | Driskell | |
| 4,645,453 A | 2/1987 | Niznick | |
| 4,713,003 A | 12/1987 | Symington et al. | |
| 4,723,913 A | 2/1988 | Bergman | |
| 4,738,623 A | 4/1988 | Driskell | |
| 4,758,161 A | 7/1988 | Niznick | |
| 4,826,434 A | 5/1989 | Krueger | |
| 4,863,383 A | 9/1989 | Grafelmann | |
| 4,932,868 A | 6/1990 | Linkow et al. | |
| 4,960,381 A | 10/1990 | Niznick | |
| 4,976,739 A * | 12/1990 | Duthie, Jr. | 606/60 |
| 5,000,686 A | 3/1991 | Lazzara et al. | |
| 5,007,835 A | 4/1991 | Valen | |
| 5,061,181 A | 10/1991 | Niznick | |
| 5,062,800 A | 11/1991 | Niznick | |
| 5,071,350 A | 12/1991 | Niznick | |
| 5,074,790 A | 12/1991 | Bauer | |
| 5,076,788 A | 12/1991 | Niznick | |
| RE33,796 E | 1/1992 | Niznick | |
| 5,078,607 A | 1/1992 | Niznick | |
| 5,087,201 A | 2/1992 | Mondani et al. | |
| 5,195,892 A | 3/1993 | Gersberg | |
| 5,226,766 A | 7/1993 | Lasner | |
| 5,230,590 A * | 7/1993 | Bohannan et al. | 407/113 |
| 5,328,371 A | 7/1994 | Hund et al. | |
| 5,343,391 A | 8/1994 | Mushabac | |
| 5,427,527 A | 6/1995 | Niznick et al. | |
| 5,433,606 A | 7/1995 | Niznick | |
| 5,435,723 A | 7/1995 | O'Brien | |
| 5,439,381 A | 8/1995 | Cohen | |
| 5,484,286 A | 1/1996 | Hansson | |
| 5,527,183 A | 6/1996 | O'Brien | |
| 5,571,017 A | 11/1996 | Niznick | |
| 5,580,246 A | 12/1996 | Fried et al. | |
| 5,584,629 A | 12/1996 | Bailey et al. | |
| 5,601,429 A | 2/1997 | Blacklock | |
| 5,628,630 A | 5/1997 | Misch et al. | |
| 5,639,237 A * | 6/1997 | Fontenot | 433/173 |
| 5,642,996 A * | 7/1997 | Mochida et al. | 433/174 |
| 5,674,072 A | 10/1997 | Moser et al. | |
| 5,702,445 A | 12/1997 | Branemark | |
| 5,725,375 A | 3/1998 | Rogers | |
| 5,759,034 A | 6/1998 | Daftary | |
| 5,782,918 A | 7/1998 | Klardie et al. | |
| 5,795,160 A | 8/1998 | Hahn et al. | |
| 5,810,590 A | 9/1998 | Fried et al. | |
| 5,816,812 A | 10/1998 | Kownacki et al. | |
| 5,820,374 A | 10/1998 | Simmons et al. | |
| 5,823,776 A | 10/1998 | Duerr et al. | |
| 5,823,777 A | 10/1998 | Misch et al. | |
| 5,871,356 A | 2/1999 | Guedj | |
| 5,876,453 A * | 3/1999 | Beaty | 433/201.1 |
| 5,897,319 A | 4/1999 | Wagner et al. | |
| 5,915,968 A | 6/1999 | Kirsch et al. | |
| 5,938,444 A * | 8/1999 | Hansson et al. | 433/174 |
| 5,967,783 A * | 10/1999 | Ura | 433/174 |
| 6,095,817 A * | 8/2000 | Wagner et al. | 433/173 |
| 6,116,904 A | 9/2000 | Kirsch et al. | |
| 6,129,730 A | 10/2000 | Bono et al. | |
| 6,135,772 A | 10/2000 | Jones | |
| 6,149,432 A | 11/2000 | Shaw et al. | |
| 6,200,345 B1 | 3/2001 | Morgan | |
| 6,227,859 B1 | 5/2001 | Sutter | |
| 6,273,722 B1 | 8/2001 | Phillips | |
| 6,283,754 B1 | 9/2001 | Wöhrle | |
| 6,287,117 B1 | 9/2001 | Niznick | |
| 6,312,259 B1 | 11/2001 | Kvarnstrom et al. | |
| 6,315,564 B1 | 11/2001 | Levisman | |
| 6,364,663 B1 | 4/2002 | Dinkelacker | |
| 6,394,806 B1 | 5/2002 | Kumar | |
| 6,402,515 B1 | 6/2002 | Palti et al. | |
| 6,419,491 B1 | 7/2002 | Ricci et al. | |
| 6,481,760 B1 | 11/2002 | Noel et al. | |
| 6,626,671 B2 * | 9/2003 | Klardie et al. | 433/201.1 |
| 6,655,961 B2 | 12/2003 | Cottrell | |
| 6,655,962 B1 * | 12/2003 | Kennard | 433/174 |
| 6,679,701 B1 | 1/2004 | Blacklock | |
| 6,726,689 B2 | 4/2004 | Jackson | |
| 6,733,291 B1 | 5/2004 | Hurson | |
| 6,733,503 B2 | 5/2004 | Layrolle et al. | |
| 6,769,913 B2 | 8/2004 | Hurson | |
| 6,913,465 B2 | 7/2005 | Howlett et al. | |
| 6,955,258 B2 | 10/2005 | Howlett et al. | |
| 7,014,464 B2 | 3/2006 | Niznick | |
| 7,108,510 B2 | 9/2006 | Niznick | |
| 7,249,949 B2 | 7/2007 | Carter | |
| 7,273,373 B2 | 9/2007 | Horiuchi | |
| 7,281,925 B2 | 10/2007 | Hall | |
| 7,383,163 B2 | 6/2008 | Holberg | |
| 8,016,594 B2 | 9/2011 | Ferris et al. | |
| 2002/0102518 A1 | 8/2002 | Mena | |
| 2002/0106612 A1 | 8/2002 | Back et al. | |
| 2002/0177106 A1 | 11/2002 | May et al. | |
| 2005/0214714 A1 | 9/2005 | Wohrle | |
| 2005/0260540 A1 | 11/2005 | Hall | |
| 2005/0287497 A1 | 12/2005 | Carter | |
| 2006/0172257 A1 | 8/2006 | Niznick | |
| 2006/0183078 A1 | 8/2006 | Niznick | |
| 2007/0099153 A1 | 5/2007 | Fromovich | |
| 2008/0014556 A1 | 1/2008 | Neumeyer | |
| 2008/0032264 A1 | 2/2008 | Hall | |
| 2008/0261175 A1 | 10/2008 | Hurson | |
| 2008/0261176 A1 | 10/2008 | Hurson | |
| 2009/0305192 A1 | 12/2009 | Hall | |

FOREIGN PATENT DOCUMENTS

| | | | |
|---|---|---|---|
| DE | 10231 743 B4 | 3/2005 | |
| EP | 0475358 A1 | 3/1992 | |
| EP | 0 707 835 A1 | 10/1995 | |
| EP | 0 707 835 B1 | 4/1996 | |
| EP | 1 396 236 A | 3/2004 | |
| EP | 1 728 486 A | 12/2006 | |
| FR | 2 600 246 | 12/1987 | |
| FR | 2610512 * | 12/1988 | A61F 2/30 |
| JP | 8-501962 | 3/1996 | |
| JP | 3026125 | 4/1996 | |
| JP | 3026125 U | 7/1996 | |
| JP | 10-052445 | 2/1998 | |
| JP | 11-502454 | 3/1999 | |
| JP | 2000-504607 | 4/2000 | |
| WO | WO 94/07428 | 4/1994 | |
| WO | WO 94/07428 A1 | 4/1994 | |
| WO | WO 94/09717 | 5/1994 | |
| WO | WO 9409717 A1 | 5/1994 | |
| WO | WO 95/09583 | 4/1995 | |
| WO | WO 9509583 A1 | 4/1995 | |
| WO | WO 95/12369 | 5/1995 | |
| WO | WO 96/16611 | 6/1996 | |
| WO | WO 97/05238 | 2/1997 | |
| WO | WO 99/23971 A1 | 5/1999 | |
| WO | WO 00/00103 A1 | 1/2000 | |
| WO | WO 00/03657 | 1/2000 | |
| WO | WO 00/62831 | 10/2000 | |
| WO | WO 00/72775 | 12/2000 | |
| WO | WO 00/72777 A1 | 12/2000 | |
| WO | WO 01/49199 | 7/2001 | |
| WO | WO 0174412 A1 | 10/2001 | |
| WO | WO 0176653 A1 | 10/2001 | |
| WO | WO 03/013383 | 2/2003 | |
| WO | WO 03/015654 | 2/2003 | |
| WO | WO 03/030767 A | 4/2003 | |
| WO | WO 03/034951 | 5/2003 | |
| WO | WO 03/055405 A1 | 7/2003 | |
| WO | WO 03/055406 A1 | 7/2003 | |
| WO | WO 03/059189 | 7/2003 | |
| WO | WO 03/061510 | 7/2003 | |
| WO | WO 03/063085 | 7/2003 | |

(56) References Cited

FOREIGN PATENT DOCUMENTS

| WO | WO 2004/098442 | 11/2004 |
|---|---|---|
| WO | WO 2004/103202 | 12/2004 |
| WO | WO 2005/117742 A1 | 12/2005 |

OTHER PUBLICATIONS

Translation of FR 2610512 retreived May 14, 2010 from EPO website.*

Mar. 11, 2004 International Search Report, Application No. PCT/SE 2003/001973, 3 pages.

3.8D series Threaded Implant, dental implant sold before Sep. 27, 1999, Nobel Biocare.

English translation of WO 2005/117742 to Neumeyer, Dec. 15, 2005.

International Search Report dated Sep. 28, 2004, for Application No. EP04734484 filed May 23, 2004. Publication No. EP 1624826 A1, published Feb. 15, 2006.

International Preliminary Report on Patentability dated Nov. 25, 2005 for PCT Application No. PCT/IL2004/000438 filed May 23, 2004. Publication No. WO 04/103202 A1 published Dec. 2, 2004.

Niznick, Gerald A., DMD, MSD. "Proactive Nobel Active New Presentaion," Implant DirectTM, Oct. 16, 2007.

Supplementary European Search Report dated May 3, 2007, for Application No. EP04734484 filed May 23, 2004. Publication No. EP 1624826 A4, published May 30, 2007.

* cited by examiner

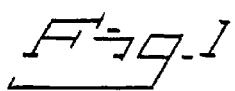
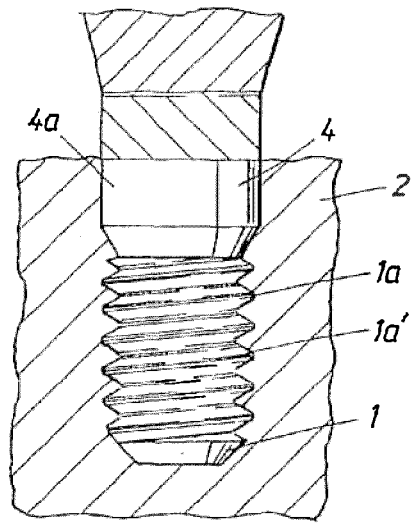
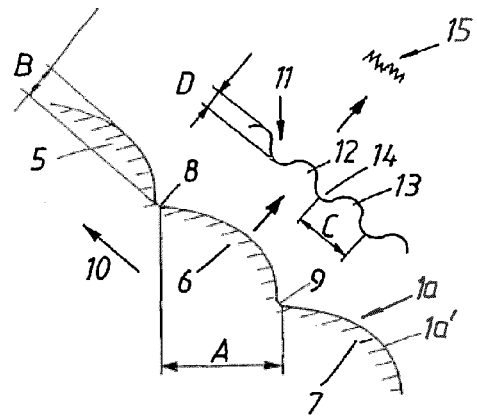
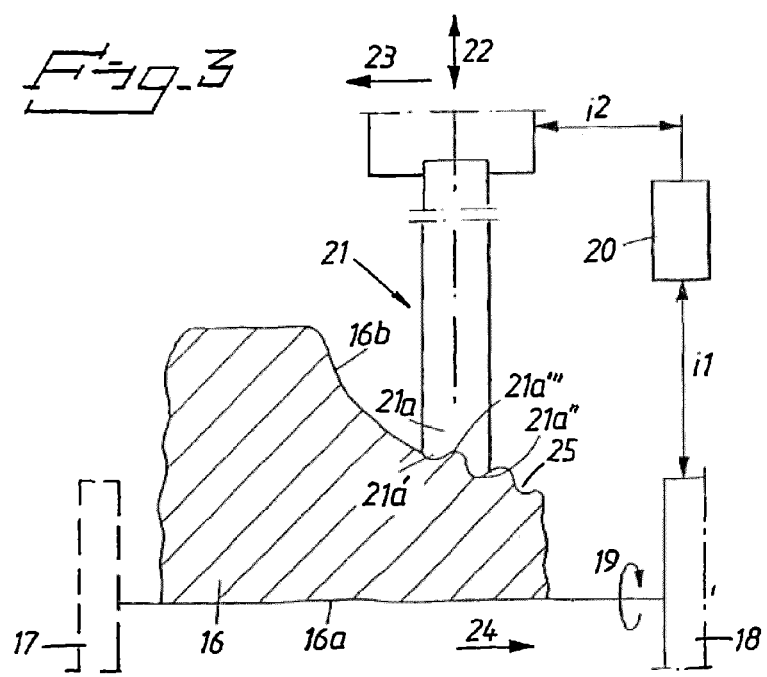

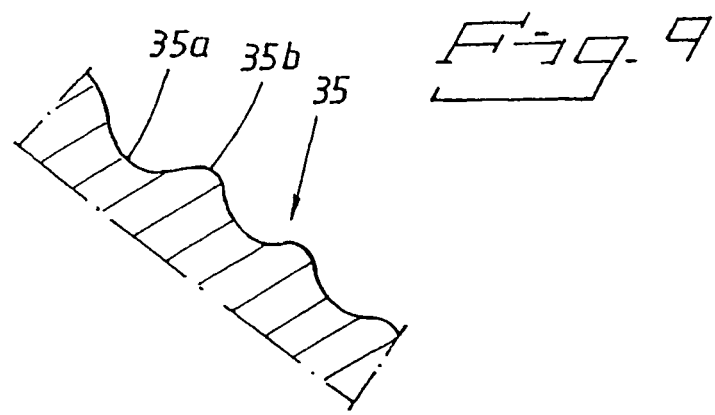
Fig. 9
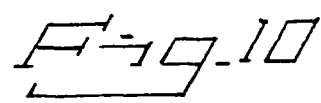
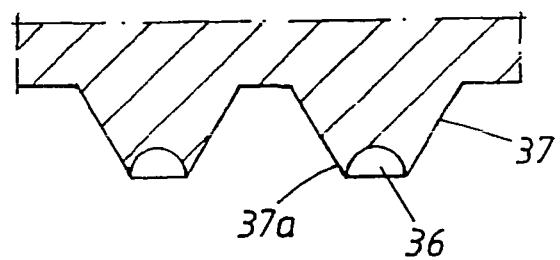
Fig. 10
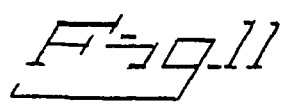
Fig. 11
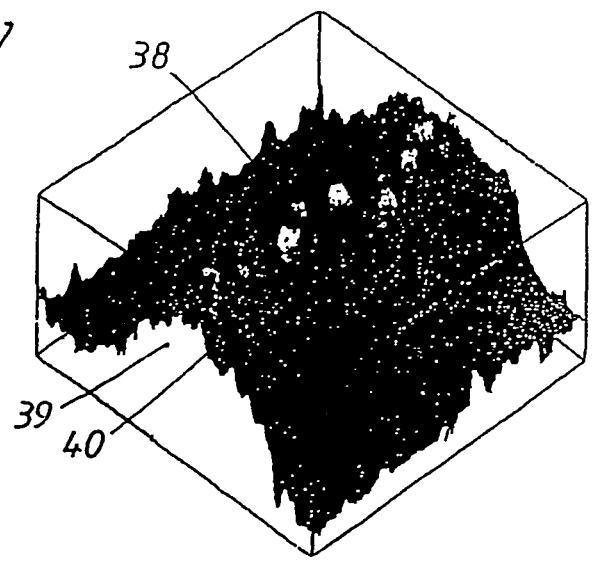

METHOD FOR PRODUCING A SURFACE STRUCTURE ON AN IMPLANT, AND SUCH AN IMPLANT

PRIORITY INFORMATION

This application is a U.S. National Phase of International Application No. PCT/SE02/02361, filed Dec. 18, 2002, which claims the benefit of Swedish Application No. 0104350-4, filed Dec. 21, 2001.

The present invention relates to a method for producing a surface structure on an outer surface of an implant or a fixture, preferably an outer surface structure which forms a base structure in a range of implants related to different types and qualities of bone, for example jaw bone. During production of the surface, parts of a tool, for example a turning tool, milling tool or shot-peening tool, are brought into cooperation with the implant or with a blank which is intended to form the implant, and at the same time the parts and/or the implant or blank are assigned controls which give rise to mutual displacements between the parts and the implant or blank so that the parts follow a substantially spiral trajectory along the surface or outer surface in question. The invention also relates to an implant which has a surface, preferably an outer surface, having a surface structure which forms a base structure in a range of implants related to different types and qualities of bone, for example jaw bone. The surface in question, preferably the outer surface in question, is arranged to cooperate with parts of a tool which can be applied to the surface, for example a turning tool, for cutting work. The outer surface is also arranged to take part in or execute a movement function together with said parts in order, depending on the controls, to allow the parts to follow a spiral trajectory along the surface in question.

In connection with the method and the implant, and with respect to the mutual movements between the parts and the implant, the parts can in principle be stationary and the implant movable, for example displaceable and/or rotatable in relation to the parts. Alternatively, the parts in question can execute the movements in relation to a stationary implant or fixture. In the third embodiment, the parts and also the implant move in the mutual movements.

The present invention is based on one or more outer surfaces of an implant being provided with an arrangement comprising a surface pattern which has been produced by cutting work, for example turning, milling or shot-peening. Reference may be made to the prior art and quite generally to the patent literature which specifies such surface patterns on cylindrical, cone-shaped and/or threaded outer surfaces.

In connection with such an outer surface which has been produced by cutting work, it has also been proposed that porous oxide layers on, for example, titanium material can be used to stimulate bone growth when an implant is fitted in bone. In one embodiment, the present invention proposes that the outer surface with a pattern produced by cutting work be combined with oxide layers. There are a great many proposals for oxide layer structures, and reference may be made inter alia to the patents obtained by the Applicant of the present patent application and to the patent applications made: SE 97 01872-5, SE 99 01971-3, SE 99 01974-7, SE 00 01201-3 and SE 00 01202-1. Reference may also be made quite generally to U.S. Pat. No. 4,330,891 (Brånemark) and EP 676179.

As far as oxide layers are concerned, a number of known oxide constructions have been proposed to function on their own in cooperation with bone or soft tissue, and a number of known oxide constructions have additionally been proposed to function as carriers of bone growth-stimulating substance. Reference may be made to the abovementioned patents and patent applications and to the patents obtained by the same Applicant and the patent applications filed: SE 99 01972-1, SE 99 01973-9, SE 01 02388-6, SE 01 02389-4, SE 01 02390-2, SE 01 02391-0 and SE 97 01647-1. Reference may also be made to the patents, patent applications and publications cited in said patents and patent applications.

The production of microfabricated outer surfaces on implants has also been discussed in SE 98 01188-5 (from the same Applicant as the present application), U.S. Pat. No. 5,588,838, EP 720454 and EP 475358. In a further embodiment according to the present invention, said layers which have been produced by cutting work are also to be combined with layers which are made in another way, for example with the aid of laser bombardment, which is also known per se.

In connection with the fitting of implants, there is a considerable requirement to be able to achieve optimum and high-quality implant results. There is a need to have access to a large number of parameters which can be exploited in different patients and different implantation situations. Given the demands of patients and treatment personnel, not all parameters can be applied in different cases. The bone quality, the patients' attitude, costs, etc., can be limiting factors, and even if development work and proposals permitting good results are moving in one direction, there may be a need for alternative solutions to be offered or used in different individual cases. Thus, for example, there may be a need to avoid bone-growth-stimulating substances but still use the associated oxide layers together with specific underlying layers. The present invention aims, inter alia, to solve this problem and proposes a unique surface layer structure produced by cutting work carried out on a cylindrical, cone-shaped and/or threaded outer surface or base surface or starting surface of an implant or fixture.

The present invention is based on the idea of achieving substantial stability of the implant incorporation in the bone in a short time, for example after just 1 to 5 days. The invention solves this problem too. In one embodiment, it is important to prevent or counteract bacterial growth at the parts where the implant emerges from the bone, for example the jaw bone. There is also a need to be able to obtain the surface pattern in question using an economical technique. This problem too is solved by the invention.

The feature which can principally be regarded as characterizing the method is that the initially mentioned control function is used to form a long wave pattern with successive peaks and with one or more troughs lying between these, or troughs surrounded by peaks. Thus, for example, a trough is obtained which extends along the outer parts of a thread. The control function is chosen so that it produces trough depths in the range of 25 to 250 µm, preferably in the range of 50 to 200 µm.

In embodiments of the novel method, one, two or more parallel troughs are formed upon said cooperation between the parts and the implant or blank. On threaded outer surfaces, the troughs are given courses which substantially follow the spiral course of the threads. In the range of implants mentioned in the introduction, the outer surfaces of the different implants are provided with different wave patterns, that is to say with different trough depths and/or peaks.

The feature which can principally be regarded as characterizing the novel implant (or the novel fixture) is that the surface in question, preferably in the form of an outer surface, has a long wave pattern formed by said control and movement function and with successive peaks or troughs separated by intermediate troughs or peaks, respectively. In this connection, a thread can be provided at its outer parts with a trough surrounded by peaks. The trough depths are in the range of 25 to 250 μm, preferably in the range of 50 to 200 μm.

In one embodiment, two or more troughs between the peaks can extend substantially parallel along the spiral trajectory. At the threaded outer surface, the troughs follow the spiral course of the thread, and the long wave pattern can be regular or can vary along the direction of its extent, that is to say in the direction substantially coinciding with the main direction of the implant. In one embodiment, the trough depths can be different or, in another embodiment, identical along the spiral course(s) of the trough or troughs. In the case of one or two or more troughs extending in parallel or alongside one another, it is possible, in a further embodiment, for the trough depth to be different. With different implants from the range of implants, these can be arranged with different long wave patterns, that is to say with different trough depths and/or peaks.

Further embodiments of the novel implant are set out in the dependent claims regarding the implant.

By means of what has been proposed above, important combination elements to the already known technique are obtained in order to obtain implant situations which are well adapted to the patients and individualized. The technique of turning as such is already known and is well proven and can be used in connection with the novel method and the novel implant. By this means, technically reliable and economically advantageous arrangements are obtained for producing combination elements and placing them on the market.

Figure 5:
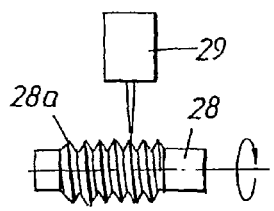
Figure 6:
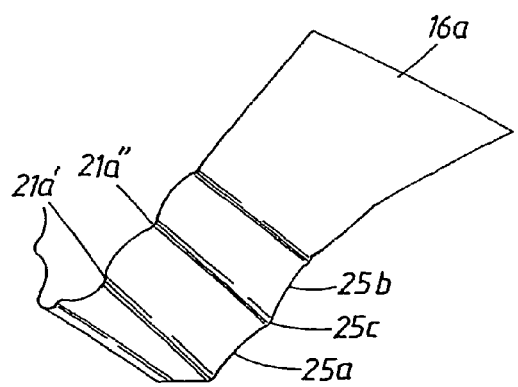
Figure 7:
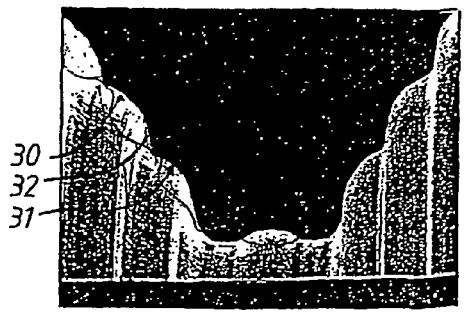
Figure 8:
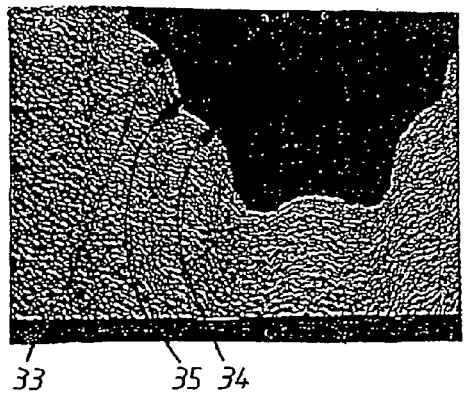

A presently proposed embodiment of a method and an implant according to the invention will be described below with reference to the attached drawings, in which FIG. 1 shows an example of an implant of the type in question which has been fitted in the jaw and has been connected to a prosthetic structure, which is indicated symbolically, FIG. 2 shows a diagrammatic view, from the side, of a base structure produced by cutting work on an implant surface of the type in question, which base structure has been provided with a wave pattern arrangement lying on top, on which wave pattern arrangement a further wave pattern and/or layer arrangement has been produced in turn, FIG. 3 shows in a side view, and in cross section, the principle for producing a wave pattern by means of cutting work (turning), FIG. 4 shows, diagrammatically and symbolically, an arrangement for applying or establishing an oxide layer on an implant which has been treated by means of cutting work, FIG. 5 shows, diagrammatically and symbolically, the application of a layer on top of the layer according to FIG. 3 which has been produced by cutting work, the layer on top being produced with the aid of a laser technique by means of which a laser bombardment is effected on the implant surface or fixture surface in question, FIG. 6 shows, in a perspective view, obliquely from above, an example of parts which cooperate with an implant or a blank for producing the implant so as to form the base structure on the surface/outer surface in question, FIG. 7 shows, in a side view, parts of an outer surface or thread of an implant provided with peaks and with troughs lying between these, with a trough depth of ca. 125 μm, FIG. 8 shows, in a side view, parts of the outer surface or outer thread of an implant which has been machined according to FIG. 7 and which has been acted on by laser bombardment and anodic oxidation, FIG. 9 shows, in partial longitudinal section, the inverted structure of troughs and peaks of an underlying wave pattern compared with the case according to FIG. 2, FIG. 10 shows, in partial longitudinal section, the application of troughs on the outer parts of a thread, and FIG. 11 shows, in a perspective view, obliquely from above, the oxide layer structure on a base structure produced by cutting work according to FIG. 3.

In FIG. 1, an implant or a fixture is indicated by 1. The implant is fitted in a jaw bone in a manner known per se, and a prosthetic structure which can be of a type known per se is applied on the upper end of the implant or the end facing away from the jaw bone. The implant is of the type which comprises an outer thread 1a, the outer surface of the implant or of the thread being indicated by 1a. The part of the implant emerging from the jaw bone 2 is indicated by 4. The implant can be part of a range of implants with different types of outer surfaces, threads, and different numbers of threads, etc. The outer surface structure must be designed so that effective growth of the surrounding bone onto the outer surface can take place and can be stabilized in a relatively short time. In accordance with the above, there is a need to have different surface structures on the outer surface 1a' interalia. The outer surface structure can vary along the longitudinal direction of the implant and thus, for example, there may be a need for the outer surface 4a of the emerging part 4 to be provided with a lower roughness value than the outer surface 1a' in order to prevent growth of bacteria on the emerging part.

The thread 1a with associated outer surface 1a' is shown greatly enlarged in FIG. 2. According to FIG. 2, the outer surface in question is to be designed as a wave pattern or with wave-shaped topography. In FIG. 2, three peaks, ridges, waves, etc., succeeding one another in the wave pattern are indicated by 5, 6 and 7. The peaks are connected via troughs 8 and 9. The wave pattern is long-wave and the waves 5, 6, 7 are each chosen with a wave length A of 25-250 μm. The troughs in question can have a trough depth B of between 25 and 250 μm. The distances A and depths B can be the same or differ along the direction of extent of the wave pattern, which in FIG. 2 is indicated by 10. In one illustrative embodiment, the outer surface 1a' can be arranged with two or more wave patterns and/or layers lying on top. Thus, for example, a wave pattern 11 with intermediate-length waves can be applied or arranged on the surface 1a'. The pattern 11 lying on top is shown greatly enlarged in relation to the underlying wave pattern which in this way forms a base structure. In the intermediate-length wave pattern 11, two peaks are indicated by 12 and 13, and a trough arranged between the peaks is indicated by 14. The wave length C is in this case chosen with a lower limit of for example 10 μm (the pit diameters can be from 75 to 150 μm). The trough depth D in this case assumes a lower value than B. Alternatively, a top layer 15 preferably consisting of an oxide layer can be arranged on the underlying wave pattern. The oxide layer 15 is shown greatly enlarged in relation to the underlying wave pattern 5, 6, 7 and the wave pattern 11 lying between. The oxide layer can be of a known type, see for example the references mentioned above. In one embodiment, all three wave patterns and layers can be present, in which case the base structure is formed by a long wave pattern, the intermediate structure by an intermediate-length wave pattern, and the outer layer 15 is formed by an oxide layer (for example of titanium).

FIG. 3 is intended to show the principles of production of the underlying base structure obtained by cutting work, said cutting work shown in the present illustrative embodiment being in the form of turning. An implant or a blank which is intended to form the implant has been shown partially by 16. The implant is arranged in a machine 17, 18 which in a manner known per se can give the implant or the blank 16 a rotational movement 19 about the longitudinal axis 16a of the implant or blank. The machining equipment in question includes a control unit 20, a turning tool is symbolized by 21, and its front or free end which can cooperate with the outer surface 16b of the implant or blank is shown by 21a. Since the equipment can be of a type known per se, it will not be described here; only the cooperation which takes place between the parts 21a and the outer surface 16b will be described in principle. The tool 21, 21a and the implant or blank can be assigned a mutual movement function. The control unit controls the movement function between the implant/blank and the turning tool 21, 21a. The control function of the control unit with respect to the equipment 17, 18 is indicated by i1, and the control function with respect to milling is indicated by i2. The implant or blank can thus be rotated about the axis 16a, and the turning tool 21, 21a can be actuated upwards and downwards in the directions of the arrows 22 as the trough formation proceeds. The control unit 20 can also assign the turning tool a displacement movement 23 along said axis of rotation 16a. In addition or as an alternative to this, the implant or blank can be displaced by controls from said control unit in its longitudinal direction, symbolized by 24. It will be seen that a continuous turning can be carried out on the outer surface 16b as a function of the chosen movement pattern controlled by the control unit. The parts 21a of the turning tool can be provided with two front parts 21a', 21a" which produce said trough arrangement 25 as the movement pattern is effected by the implant/blank and the turning tool 21. Said front parts 21a' and 21a" produce two parallel troughs which follow a spiral trajectory along the outer surface 16b of the implant or blank. The spiral shape is dependent on the mutual movement function, and the trough formation or wave pattern formation can be effected on the given outer surface on a cylindrical, cone-shaped and/or threaded outer surface of the implant or blank. As regards the trough pattern, reference is made to FIG. 2 and the peaks 5, 6 and 7 and intermediate troughs 8 and 9 indicated there. The trough depths B are thus determined by the front parts 21a' and 21a". The shapes and lengths of the peaks are determined by means of a part 21a''' which lies between said front parts. The turning tool can have another design, in which case, however, the described principle is preferably used. In addition, the turning tool can be given oscillating movements in the main radial direction(s) of the implant.

In accordance with what has been stated above, the long wave pattern thus established in FIG. 3 can be provided with a top oxide layer in a manner known per se. FIG. 4 indicates the principle of applying an oxide layer on an implant 26 which has been provided with a base structure 26a in accordance with the above. The oxide application or oxide production on the layer produced by cutting work takes place in a manner known per se in an oxidation unit 27 known per se, in which connection reference may be made to the above-mentioned prior art.

FIG. 5 is intended in principle to show how an intermediate layer according to FIG. 2 can be applied on an implant which has been provided with an underlying wave pattern or with an underlying base structure according to FIG. 3. In this case, the implant has been indicated by 28, and the layer lying on top has been indicated by 28a. Laser bombardment equipment is known per se in connection with implants of this type, and such equipment has been indicated diagrammatically by 29. In an alternative embodiment, the implant 26 in FIG. 4 can represent an implant provided with two layers according to FIGS. 3 and 5, in which case the outer layer which has been produced in accordance with FIG. 5 is provided with the oxide layer 26 a in question in the oxidation unit 27.

FIG. 6 shows the turning tool 21 in a perspective view, obliquely from above, in relation to the surface of the implant or blank 16. Two successive peaks are indicated by 25a and 25b, and a trough located between the peaks is indicated by 25c.

FIG. 7 shows an illustrative embodiment of the application of a long wave pattern on a thread arrangement of an implant. Successive waves or peaks have been indicated by 30 and 31, and a trough lying between these, of the order of size of 125 µm, is indicated by 32.

FIG. 8 shows a wave pattern according to 11 in FIG. 2 which is applied on an underlying wave pattern or an underlying base structure where successive waves have been indicated by 33 and 34 and an intermediate trough arrangement has been indicated by 35. The top wave pattern according to 11 in FIG. 2 consists of a pattern produced by laser equipment, and the underlying base structure has troughs with depths of ca. 75 µm. An oxide layer is additionally arranged on said top wave pattern.

FIG. 9 is intended to show, at 35, the inverted structure of the wave pattern compared with FIG. 7, where 35a shows the troughs and 35b the peaks. In FIG. 10, reference number 36 indicates a trough arranged at or on a thread 37 whose outer parts (or edge) have been shown by 37a.

FIG. 11 shows, obliquely from outside, an oxide layer 38 which is arranged on the base structure according to FIG. 7, but where the trough depth is ca. 75 µm instead of ca. 125 µm. The oxide layer topography in question can be designed in a manner known per se in accordance with the above and the prior art. In FIG. 11, a peak on the base structure is shown by 39, and the parts of the oxide layer cooperating with the base structure are shown by 40. The layer 38 has a known pore structure and has a depth of 0.01 to 10 µm, preferably 1 to 4 µm.

The invention is not limited to the illustrative embodiment given above by way of example, and instead it can be modified within the scope of the attached patent claims and the inventive concept. Reference is also made to the Swedish patent application filed on the same day and by the same Applicant and bearing the title "Implant, and method and system for producing such an implant".

The invention claimed is:

1. A method for producing a surface structure on a dental implant, the method comprising:
   cooperating parts of a tool with a blank which is intended to form the dental implant;
   assigning controls which give rise to mutual displacements between the parts and the blank so that the parts follow a substantially spiral trajectory along a surface of the blank; and
   forming a thread on the surface of the blank, the thread when seen in side view comprising an outer surface and a wave pattern with at least one trough disposed on the outer surface of the thread, the trough extending in a course that substantially follows a spiral trajectory of the thread, the wave pattern when seen in side view extending along the outer surface of the thread in a generally longitudinal direction of the implant, wherein the trough depth is in the range of between approximately 25 to 200 µm.

2. The method as in claim 1, wherein forming said thread comprises forming the wave pattern comprising at least two parallel troughs, which are formed by said cooperation between the parts of the tool and the blank.

3. The method as in claim 1, wherein at least one trough is given a course which follows a spiral course of the thread along a crest of the thread.

4. The method as in claim 1, comprising forming a set of different implants, the outer surfaces of the different implants including cylindrical, cone-shaped or threaded portions, having different wave patterns with different trough depths with respect to other implants in the set.

5. The method as in claim 1, wherein the trough depth is approximately 75 μm.

6. The method as in claim 1, further comprising forming an intermediate wave pattern on the wave pattern formed along the outer surface of the thread when seen in side view, the intermediate wave pattern having a wave length less than the wave length of the long wave pattern.

7. The method as in claim 6, further comprising forming an oxide layer on the surface of the dental implant.

8. The method as in claim 1, wherein forming said thread comprises removing material from said blank.

9. The method as in claim 1, wherein forming said thread comprises producing said thread by one of turning, milling, and shot-peening.

10. The method as in claim 1, wherein forming said thread comprises producing a repeated wave pattern.

11. The method as in claim 10, wherein producing the repeated wave pattern comprises producing three waves each having a trough.

12. The method as in claim 1, wherein the wave pattern comprises a pair of troughs that extend generally parallel relative to each other substantially following the spiral trajectory of the thread along the outer surface of the thread.

13. The method as in claim 1, wherein the trough has a depth of between approximately 50 to 150 μm.

14. The method as in claim 13, wherein the trough has a depth of approximately up to 75 μm.

15. A dental implant comprising:
an implant body defining a longitudinal axis and an exterior surface; and
a thread extending about the implant body in a spiral trajectory, the thread defining an outer surface, wherein when seen in side view, the outer surface of the thread comprises a wave pattern with at least one trough, the wave pattern extending generally in the direction of the longitudinal axis of the implant body, the trough extending in a course that substantially follows the spiral trajectory of the thread, the wave pattern having a respective trough depth in the range of between approximately 25 to 200 μm.

16. The implant as in claim 15, wherein the wave pattern includes at least two troughs that extend substantially parallel along the spiral trajectory.

17. The implant as in claim 15, wherein the troughs of the wave pattern follow the spiral trajectory of the thread along a crest of the thread.

18. The implant as in claim 15, wherein the wave pattern varies along the implant.

19. The implant as in claim 15, wherein the trough varies along the spiral trajectory.

20. The implant as in claim 15, wherein the wave pattern includes at least two troughs running alongside one another, the troughs having different depths.

21. The implant as in claim 15, wherein the implant forms part of a set of implants, the set including implants with wave patterns having different trough depths.

22. The implant as in claim 15, wherein the wave pattern forms a base structure for a second wave pattern having a wave length less than a wave length of the wave pattern, the second wave pattern being applied on the wave pattern.

23. The implant as in claim 15, wherein the wave pattern forms a base structure for an oxide layer produced on the wave pattern.

24. The implant as claim 15, wherein the wave pattern forms a base structure for both a second wave pattern having a wave length less than the wave pattern and a formed layer located on top of the intermediate wave pattern.

25. The implant as in claim 15, wherein the implant forms part of a set of implants, the implants in the set having a range of wave pattern structures for complying with a specific jaw bone structure.

26. The implant as in claim 15, wherein the wave pattern is formed by laser bombardment.

27. The implant as in claim 15, wherein the trough depth is approximately 75 μm.

28. The implant as in claim 15, wherein the wave pattern comprises three waves each having a peak and a trough.

29. The implant as in claim 15, wherein the wave pattern comprises a pair of troughs that extend generally parallel relative to each other substantially following the spiral trajectory of the thread along the outer surface of the thread.

30. The implant as in claim 15, wherein the trough has a depth of between approximately 50 to 150 μm.

31. The implant as in claim 30, wherein the trough has a depth of approximately up to 75 μm.

32. The implant as in claim 15, wherein the at least one trough of the wave pattern extends along an apex of the thread.

33. The implant as in claim 15, wherein the at least one trough of the wave pattern extends along a flank of the thread.

* * * * *